United States Patent [19]

Speranza et al.

[11] Patent Number: 5,206,362
[45] Date of Patent: Apr. 27, 1993

[54] TWO-STEP METHOD FOR PREPARING CYCLIC UREAS

[75] Inventors: George P. Speranza, Austin; Donald H. Champion, Pflugerville, both of Tex.

[73] Assignee: Texaco Chemical Company, White Plains, N.Y.

[21] Appl. No.: 837,131

[22] Filed: Feb. 19, 1992

[51] Int. Cl.$^5$ .................. C07D 413/12; C07D 14/06
[52] U.S. Cl. .................. 540/454; 540/451; 540/464
[58] Field of Search .................. 540/454, 451, 464

[56] References Cited

U.S. PATENT DOCUMENTS 3,763,106 10/1973 Markiewitz .................. 540/454
5,051,503 9/1991 Schlight .................. 540/454

OTHER PUBLICATIONS

L. Birkofer et al., *Chem. Ber.*, 93, 2810 (1960).
A. V. Bogatsky, *Synthesis*, 1982, 464.
*J. Heterocyclic Chem.*, 10, 6 39 (1973).
N. G. Lukyanenko, *Synthesis*, 1986, 928.
J. Michels, *J. Org. Chem.*, 25, 2246 (1960).
S. Ozaki et al., *J. Am. Chem. Soc.*, 79, 4358 (1957).

*Primary Examiner*—Floyd D. Higel
*Attorney, Agent, or Firm*—James L. Bailey; Kenneth R. Priem; Cynthia L. Kendrick

[57] ABSTRACT

Disclosed is a two-step method for the preparation of cyclic urea products which comprises: heating a diamine with urea in a mole ratio of about 1 at a temperature from about 120° C. to 140° C. until a mole of ammonia is liberated and slowly heating the intermediate with an alcohol or polyether solvent to a temperature from about 160° C. to 200° C. to produce the cyclic urea products.

12 Claims, No Drawings

TWO-STEP METHOD FOR PREPARING CYCLIC UREAS

FIELD OF THE INVENTION

This invention relates to cyclic ureas. More particularly this invention relates to an economical two-step method of preparing large ring cyclic urea products from commercially available reactants which comprises heating a diamine with urea at a temperature in the range from about 110° C. to 140° C. until 1 mole of ammonia is liberated, adding a solvent to the intermediate product and heating the mixture to a temperature from about 170° C. to 200° C.

This method provides a very efficient and cost effective means of producing large ring cyclic ureas from commercially available diamines.

BACKGROUND OF THE INVENTION

The preparation of cyclic ureas is known in the art. Cyclic ureas of 5, 6 and 7 membered atoms are not difficult to prepare. They are often synthesized by the reaction of diamines with phosgene, urea or carbon dioxide. Methods for the preparation of higher molecular weight cyclic products are complicated by the side reaction of linear polycondensations. (See G.A. Settepani et al, *J. Heterocyclic Chem.* 10,639 (1973); J. Michus, *J. Org. Chem.* 25, 2246 (1960); L. Birkofer et al., *Chem. Ber.* 93, 2810 (1960).

Large ring cyclic ureas can also be prepared by careful reaction of diisocyanates with water utilizing a high dilution technique. For example, utilizing 900 ml of acetone and 900 ml of water as reaction media, 3.2 g of octamethylene diisocyanate in 70 ml of acetone was added over a 17 hour period in a special Hunsdiecker apparatus. The yield was 18%.

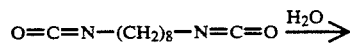

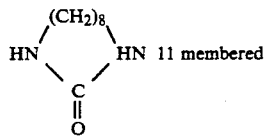

The yields increased to 49% for a 13 membered ring, 41% for a 15 membered ring and 36% for a 17 membered ring. See S. Ozaki et al., J. Am. Chem. Soc. 79, 4358 (1957)

In *Synthesis*, 1982, 464, A.V. Bogatsky et al. disclose that macrocyclic thioureas can be obtained by the reaction of carbon disulfide. Bogatsky et al. disclose that cyclic thioureas with alkyl halides in the presence of aqueous sodium hydroxide and catalytic amounts of benzyltriethylammonium chloride produce the corresponding N,N'-dialkylureas in good yields.

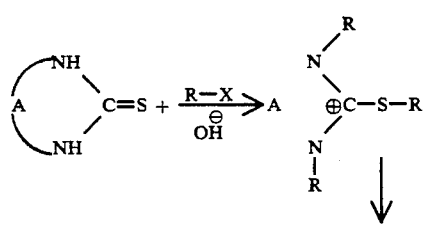

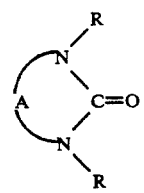

Further, they suggest cyclic N,N'-dialkylureas of 5 to 22 carbon atoms could be prepared using this method. The macrocyclic polyoxyethylene ureas are described by this group as a new type of crown ether. Large cyclic rings allow the carbonyl groups to orient themselves into the cavity which permits coordination of a metal ion with both the ether and the carbonyl oxygen atoms. Ligands such as those below would interact with lithium, sodium and potassium ions (R=alkyl).

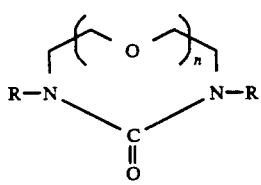

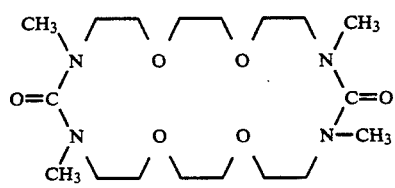

Later, N.G. Lukyanenko et al., reported in *Synthesis*, 1986, 928, that macrocyclic thioureas may be converted to macrocyclic ureas by another route which can be represented by the following:

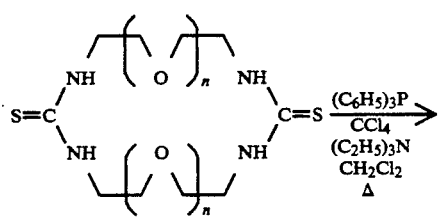

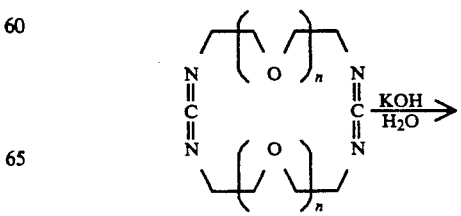

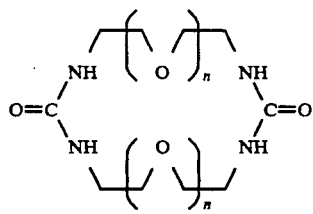

As noted, in a number of the methods for preparing cyclic ureas found in the art, disadvantages include side reactions involving linear polycondensations and the need to first prepare a diisocyanate derivative of the diamine. Cyclization of the diisocyanate requires very high dilution techniques.

U.S. Pat. No. 3,763,106 is of interest for teaching a different result using similar reactants to those which are found useful in the instant invention.

It would represent a substantial advance in the art if cyclic ureas could be prepared from commercially available reactants such as diamines and urea under very controlled reaction conditions without the necessity for high dilution techniques.

SUMMARY OF THE INVENTION

The present invention involves the preparation of large ring cyclic urea products from diamines and in particular polyoxyalkylene diamines, such as, for example, triethylene glycol diamine or tetraethylene glycol diamine, reacted with urea at a temperature in the range from about 120° C. to 140° C. until 1 mole of ammonia is liberated, and subsequently reacting the intermediate in a polyether or alcohol solvent at a temperature in the range from about 170° C. to 190° C.

DETAILED DESCRIPTION OF THE INVENTION

In the instant invention a simple procedure has been discovered for the preparation of macrocyclic ureas which does not involve the use of carbon disulfide nor the need to prepare a diisocyanate derivative of the diamine. In addition, the instant procedure does not require extremely high dilution techniques often associated with the preparation of macrocyclic rings. The first step in the procedure calls for the addition of urea to the diamines under controlled reaction conditions. In the second step the intermediate product is slowly heated with a solvent. The method can be represented by the following:

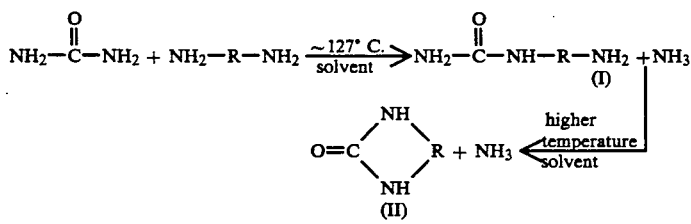

where R is selected from: R=(CH$_2$)$_x$ where x=10-22 and

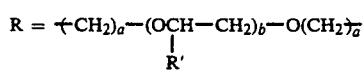

or

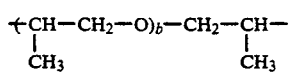

where a=2 or 3, b=2–4 and R'=CH$_3$ or H.

The temperature range which is effective in the first step of the method of this invention is from about 120° C. to 150° C. The preferred range is between about 120° C. and 135° C. It is noted in Examples 1, 2, 5, 8 and 9 that ammonia evolved around 125°–128° C.

After a mole of ammonia has evolved the intermediate is reacted in a second step in a polyether or alcohol solvent to form the large ring (cyclic) urea. The product (I) is added slowly to a solvent that is heated to about 180° C. The addition usually takes place over several hours, i.e. from about 2 to 10 hours, at or near the boiling point of the solvent to complete the reaction.

Generally, the solvent should be an alcohol or ether. Alcohols which work include 2-ethylhexanol, dipropylene glycol, dipropylene glycol monomethylether and dipropylene glycol monoethylether. Example 6 demonstrates the usefulness of 2-ethylhexanol.

The solvent in the instant invention can also be a polyether, including diethylene glycol diethylether, triethylene glycol dimethylether (triglyme). More preferable is the use of a methylated product of a polyether alcohol, such as, for example, diglyme and triglyme. The examples demonstrate the effectiveness of triglyme.

One aspect of the instant invention which makes it quite desirable is that the large ring cyclic ureas can be prepared from commercially available reactants, such as long chain diamines and polyoxyalkylene diamines.

The polyoxyalkylene amines which are particularly useful in this invention are polyethylene glycol diamines. Preferred are amine terminated polyethylene glycols having the formula:

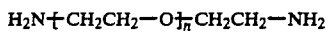

where n=2 or 3.

This includes triethylene glycol diamine and tetraethylene glycol diamine. These ar polyoxyethylene diamines produced by Texaco Chemical Company under the name JEFFAMINE ® EDR series amines. JEFFAMINE ® EDR-148 is an amine terminated triethylene glycol having the formula:

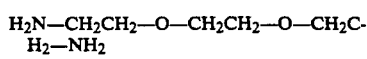

JEFFAMINE ® EDR-192 is an amine terminated tetraethylene glycol having the formula:

H$_2$N—CH$_2$CH$_2$—O—CH$_2$CH$_2$—O—CH$_2$CH$_2$—CH$_2$CH$_2$—NH$_2$

Other useful glycol diamines include polypropylene glycol diamines, such as tripropylene glycol diamine and tetrapropylene glycol diamine.

Also useful are other long chain diamines such as dodecanediamine (Example 10) and polyetherdiamines with aminopropyl end groups, NH$_2$(CH$_2$)$_3$(OCHRCH$_2$)OCH$_2$CHRO(CH$_2$)$_3$NH$_2$ (Example 8). It is recognized that other long chain diamines with primary amine end groups and (optionally) containing functional groups that are inert under the reaction conditions may be employed.

The polyoxyalkylene diamines, such as those described above, are reacted with urea, preferably in a ratio of about one mole of diamine to one mole of urea. In the instant invention it is noted that when two moles of urea is heated with one mole of triethylene glycol diamine, ammonia begins to evolve at about 128° C. On increasing the heat to 180° C. over about an 8 hour period, a good yield of the bis-urea was formed:

$$NH_2-\overset{O}{\overset{\|}{C}}-NH-(CH_2CH_2O)_2-CH_2CH_2-NH-\overset{O}{\overset{\|}{C}}-NH_2$$

In a similar fashion, when two moles of EDR-148 was heated with one mole of urea, ammonia started to release at 122° C. On heating up to 140° C. for 3 hours and heating 4 hours at 160° C. a good yield of the expected diamine was obtained:

$$NH_2+CH_2CH_2O)_2-CH_2CH_2-NH-\overset{\|}{\underset{O}{C}}-NH+CH_2CH_2O)_2-CH_2-CH_2NH_2$$

The instant invention appears to work by means of a stepwise elimination of ammonia to obtain the monocondensation products represented by:

$$NH_2-R-NH-\overset{\|}{\underset{O}{C}}-NH_2$$

where R is selected from: R=(CH$_2$)$_x$ where x=10–22 and $$R = +CH_2)_a-(OCH-CH_2)_b-O(CH_2)_a \atop R'$$

or $$+CH-CH_2-O)_b-CH_2-CH- \atop CH_3 \quad\quad\quad CH_3$$

where a=2 or 3, b=2–4 and R'=CH$_3$ or H.

The products were identified by NMR or mass spectrometry. Although the reactions are not quantitative they are sufficiently selective so that the reaction can be used to make the ring compounds in this convenient and low cost step.

The following examples ar intended to illustrate the invention in more detail, however they should not be construed as limiting the invention in any way.

EXAMPLE 1

Tetraethylene Glycol Diamine and Urea

To a 250 ml three-necked flask equipped with a thermometer, stirrer and condenser was charged 91 grams of EDR-192 (0.5 moles) and 30 grams of urea (0.5 moles). The contents were heated to 126° C. and held at 126°–127° C. for 3.25 hours. The product weighed 111.1 grams and the NMR spectrum was in good agreement with the proposed structure:

$$NH_2-\overset{O}{\overset{\|}{C}}-NH+CH_2CH_2O)_3CH_2CH_2NH_2$$

EXAMPLE 2

Cyclization

The product described above (25 g) was mixed with 125 g of triglyme and added over a three hour period to triglyme (100 g) heated at 180° C.

EXAMPLE 3

EDR-192 and Urea

The same reactants were heated as in Example 1. A total of 384 g of EDR-192 was heated with 120 g of urea at 125° C. for 2 hours. NMR showed that the average structure was $$NH_2(CH_2CH_2O)_3-CH_2CH_2NH-\overset{O}{\overset{\|}{C}}-NH_2$$

with small amounts of starting material and some bis-urea adduct. Amine analysis was 4.30 meq/g (theory 4.26 for the structure shown).

EXAMPLE 4

Cyclization

To a one-liter three-necked flask (Morton) ®quipped with a stirrer, thermometer, nitrogen inlet and dropping funnel was charged 450 ml of 2-ethylhexanol. The alcohol was heated to 182° C. and then 100 g of the product described in Example 3 and 450 ml of 2-ethylhexanol was added over a 4 hour period to the alcohol kept at 182°–184° C. On cooling some crystals separated and eventually a total of 49.4 g of solid was collected. The product was identified as the cyclic product obtained in Example II. Mass spectrometry indicated a molecular weight of 218.1282 which corresponds well with the desired product m.w. 218.1267 (C$_9$H$_{18}$N$_2$O$_4$).

EXAMPLE 5

Tetrapropylene Glycol Diamine and Urea $$NH_2-(CH-CH_2O)_3-CH_2-CH-NH_2 + \atop CH_3 \quad\quad\quad\quad CH_3$$

-continued

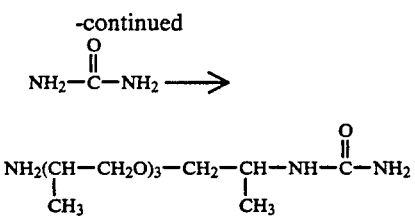

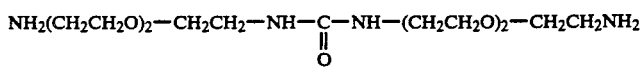

In a 100 ml flask equipped with a magnet stirrer, thermometer, condenser and nitrogen inlet, 24.8 g of tetrapropylene glycol diamine was heated with 6.0 g of urea at 127° to 128° C. for 4 hours. NMR analysis indicated that about half the amine groups reacted and most of the urea was monosubstituted. The product was a colorless viscous liquid. It had an amine assay of 2.84 meq/g; theory for pure product is 3.42.

EXAMPLE 6

Cyclization of Product from Example 5

To a 500 ml three-necked flask equipped with a stirrer, thermometer, addition funnel and nitrogen inlet was added 200 ml of 2-ethylhexanol which was heated to reflux. 19.4 g of the product obtained in Example 5 in 125 ml of 2-ethylhexanol was added over a 3 hour period. The contents were heated at reflux for an additional 2 hours and the solvent removed by distillation to obtain 20.4 g of material. Mass spectroscopic analysis showed a small amount of cyclic product with a m.w. of 274.2163 (actual m.w. of the macrocyclic is 274.1893). IR analysis indicated a mixture of products.

EXAMPLE 7

Bis(aminoethyl) Ether and Urea

Attempts to form a cyclic product from bis(aminoethyl) ether and urea were unsuccessful. Polymeric materials were formed. It is known that 7 and 8 membered ring compounds polymerize readily with heat alone.

EXAMPLE 8

Diethylene Glycol Bis(propylamine) and Urea

NH₂—CH₂—CH₂CH₂OCH₂CH₂OCH₂CH₂OCH₂CH₂CH₂NH₂ +

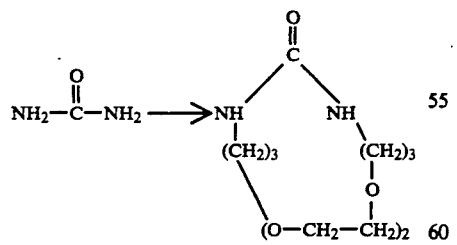

The amine (44 g) was heated with 12 g of urea at 124°-127° C. for 3 hours giving 52 g of product. This product, 25 g, dissolved in 150 ml of 2-ethylhexanol was added to 200 ml of boiling 2-ethylhexanol. (Material had to be removed from the addition funnel to keep a homogeneous solution). Most of the solvent was removed and the product washed with isopropanol. The product was difficult to filter but after getting a wet cake the solvent was removed at 70° C. and about 0.3 mm mercury pressure. The product weighed 12.2 g. Mass spectrometry showed that the monomeric cyclic product was found in good yield. The calculated m.w. was 246 15996; the actual m.w. was 246.15796.

EXAMPLE 9

Triethylene Glycol Diamine (EDR-148) and Urea 296 g of EDR-148 Were allowed to react with 120 g of urea. The urea was added to EDR-148 and heated to 80° C. over a 40 minute period. The mixture was heated to 126° C. and held at 126°-127° C. for 2 hours. NMR showed that about 17% of the product was disubstituted urea.

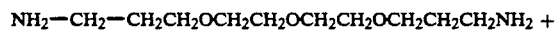

Nevertheless, 100 g of this material in 2-ethylhexanol was added to 450 ml of boiling 2-ethylhexanol over a 5 hour period. Crystals separated when the solution was cooled. A total of 92.2 g of crystals were obtained after filtering and washing twice with 250 ml of cyclohexane. The crystals were heated with isopropanol and dried to give 77.5 g of material melting ~132°-148° C. with some changes occurring below 132° C. M S indicated some of the material was the expected cyclic product: 174.1008 was detected which corresponds well with the desired product m.w. 174.1004. Attempts to sublime this material resulted in polymerization. This is not unexpected since Makacyama et al. indicated that cyclic ureas, especially those with 7 to 10 members in the ring, were thermally unstable. See J. Am. Chem. Soc. 79, 4358, 1957.

EXAMPLE 10

Dodecane Diamine and Urea

To a one liter three-necked flask equipped with a stirrer, thermometer, nitrogen inlet and condenser was charged 200 g of dodecane diamine, 400 ml of 2-ethylhexanol and 60 g of urea. The contents were heated to 127° C. and held at this temperature for three hours. On cooling the material settled to a homogeneous white cake. An additional 300 ml of 2-ethylhexanol was added and the mass heated to 105° C. Portions of this material were added to boiling 2-ethylhexanol over a five hour period. The contents were heated at 185° C. for an additional four hours, cooled to 50° C. and the solid filtered and dried. The cyclic diamine $C_{13}H_{26}N_2O$ was obtained (m.w. 226). It was contaminated with a little amine (0.085 meq/g).

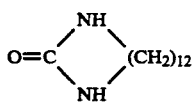

The product melted at 207°-213° C.

What is claimed is:

1. A two-step method for the preparation of a large ring cyclic urea which comprises:
   heating about one mole of a diamine having 8 to 22 carbon atoms between NH₂ groups with one mole of urea to a temperature from about 120° C. to 140° C. until 1 mole of ammonia is liberated and slowly heating the intermediate with a solvent selected from the group consisting of alcohols and polyethers to a temperature from about 160° C. to 200° C. to produce the large ring cyclic urea products.

2. The method of claim 1 wherein the diamine is a polyoxyalkylene diamine with the formula:

$$H_2N{+}CHCH_2{-}O{+}_n CH_2CH{-}NH_2$$
$$\phantom{H_2N{+}C}R\phantom{HCH_2{-}O{+}_nCH_2C}R$$

where R=H or CH$_3$ and n=2, 3, 4 or 5.

3. The method of claim 2 wherein the polyoxyalkylene diamine is a polyethylene glycol diamine with the formula:

$$H_2N{+}CH_2CH_2{-}O{+}_n CH_2CH_2{-}NH_2$$

where n=2, 3 or 4.

4. The method of claim 3 wherein the polyoxyethylene diamines are selected from the group consisting of triethylene glycol diamine and tetraethylene glycol diamine.

5. The method of claim 1 wherein the diamine is selected from the group consisting of a tetrapropylene glycol diamine and tripropylene glycol diamine.

6. The method of claim 1 wherein the diamine is dodecane diamine.

7. The method of claim 2 wherein the polyoxyalkylene diamine is a polyoxyalkylene bis(propylamine) with the formula:

$$NH_2{-}CH_2CH_2CH_2(OCH_2CH_2{-})_nOCH_2CH_2CH_2NH_2$$

where n=2 or 3.

8. The method of claim 1 wherein the reactants in the first step are heated to a temperature of about 125° C. to 130° C.

9. The method of claim 1 wherein the polyether solvent is triglyme.

10. The method of claim 1 wherein the alcohol solvent is 2-ethylhexanol.

11. The method of claim 1 wherein in the second step the intermediate and solvent are heated over a period of 2 to 10 hours.

12. The method of claim 1 wherein the intermediate and solvent are heated in the second step to a temperature between 170° C. and 190° C.

* * * * *